(12) United States Patent
Sumida et al.

(10) Patent No.: US 7,319,165 B2
(45) Date of Patent: Jan. 15, 2008

(54) AMINOPOLYCARBOXYLIC ACID AQUEOUS SOLUTION COMPOSITION AND STABILIZATION METHOD OF AMINOPOLYCARBOXLIC ACID

(75) Inventors: Yasutaka Sumida, Neyagawa (JP); Mitsuhiro Kitajima, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/458,186

(22) Filed: Jun. 11, 2003

(65) Prior Publication Data

US 2004/0171877 A1 Sep. 2, 2004

(30) Foreign Application Priority Data

Jun. 11, 2002 (JP) ............................. 2002-170205

(51) Int. Cl.
*C07C 229/00* (2006.01)
*C07C 205/00* (2006.01)
*C07C 55/00* (2006.01)

(52) U.S. Cl. ...................... 562/571; 562/553; 562/590

(58) Field of Classification Search ..................... None
See application file for complete search history.

(56) References Cited

U.S. PATENT DOCUMENTS

| 3,954,858 | A | * | 5/1976 | Lamberti et al. | ............ | 562/583 |
| 5,541,041 | A | * | 7/1996 | Haye | ........................... | 430/393 |
| 6,103,458 | A | * | 8/2000 | Seki | ........................... | 430/393 |

FOREIGN PATENT DOCUMENTS

| EP | 0 708 078 A1 | 4/1996 |
| JP | 7-224014 A | 8/1995 |
| JP | 8-169866 | 7/1996 |
| JP | 9-110812 A | 4/1997 |
| JP | 2644977 | 5/1997 |
| JP | 09208990 | * 8/1997 |
| JP | 10-87580 | 4/1998 |
| JP | 10-87582 | 4/1998 |
| JP | 10-231469 A | 9/1998 |
| JP | 2001342453 | * 12/2001 |
| JP | 2002-88034 A | 3/2002 |
| JP | 2002088034 | * 3/2002 |

OTHER PUBLICATIONS

XP-002279575 (abstract of JP10-87580); Apr. 17, 1998; Database HCAPLUS ACS; retrieved from STN; Database accession No. 128:296179/DN; abstract; RN 159753-00-1.

XP-002279576 (abstract of JP10-087582); Apr. 17, 1998; Database HCAPLUS ACS; retrieved from STN; Database accession No. 128:283911/DN; abstract; RN 159753-00-1, 172737-80-3.

* cited by examiner

*Primary Examiner*—Karl Puttlitz
(74) *Attorney, Agent, or Firm*—Connolly Bove Lodge and Hutz

(57) ABSTRACT

The present invention is to provide a stabilized aqueous aminopolycarboxylate solution composition and a method of stabilizing the aminopolycarboxylate through preventing the same from caking.

An aqueous aminopolycarboxylate solution composition containing an aminopolycarboxylate represented by the following general formula (1):

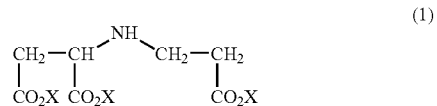

in the formula, X may be the same or different and represents a hydrogen atom, an alkali metal atom, or an ammonium group, which has a D-form/L-form molar ratio of an aspartic acid skeleton of the aminopolycarboxylate of 1/6 to 0.7/0.3 or 0.3/0.7 to 0/1, has a solid concentration of 25 to 60 mass %, and has a pH value of not more than 11.

10 Claims, No Drawings

AMINOPOLYCARBOXYLIC ACID AQUEOUS SOLUTION COMPOSITION AND STABILIZATION METHOD OF AMINOPOLYCARBOXLIC ACID

TECHNICAL FIELD

The present invention relates to an aqueous aminopolycarboxylate solution composition and a stabilization method of an aminopolycarboxylate. More particularly, the present invention relates to a stabilized aqueous aminopolycarboxylate solution composition and a method by which an aminopolycarboxylate can be handled in the form of a stable and homogeneous aqueous solution.

BACKGROUND OF THE ART

Salts of aminopolycarboxylic acids such as N-2-carboxyethyl-aspartic acid (aminopolycarboxylates) have high chelating activity sequestering metal ions and may find application as chelating agents for use in the removal of toxic metals, concentrating and recovery of valuable metals, and fractional purification of metals.

However, when handled in solid states such as powders and granules, aminopolycarboxylates absorb atmospheric moisture to form viscous masses, with the result that for use as metal chelating agents or the like, there is room for contrivance avoiding such troubles to occur. Furthermore, regarding aminopolycarboxylates of low purity, these tend to separate out in aqueous solution necessitating to hold product concentrations sufficiently low. Thus, if aminopolycarboxylates could be handled stably, these compounds should become applicable to industrial uses such as detergent builders, soap additives, textile dyeing agents, plating chemicals, auxiliary bleaches, and photographic chemicals (photographic chelating agents) for the formulation of photographic processing compositions; therefore, there is room for technological sophistication in the art of stabilizing aminopolycarboxylates.

Meanwhile, Japanese Kokai Publication Hei-08-169866 discloses a technology of handling an iminocarboxylate salt in the form of an aqueous solution controlled to the isomer ratio of the aspartic acid skeleton of said iminocarboxylate salt to D-form/L-form (molar ratio)=1/0 to 0.7/0.3 or D-form/L-form (molar ratio)=0/1 to 0.3/0.7, the concentration of said iminocarboxylate salt being controlled to 40 to 70 weight % and the pH of the solution being controlled to pH 7 to 12. Japanese Patent Publication No. 2644977 discloses an iminocarboxylate salt aqueous solution controlled to the isomer ratio of the aspartic acid skeleton to D-form/L-form (molar ratio)=1/0 to 0.7/0.3 or D-form/L-form (molar ratio)=0/1 to 0.3/0.7, the concentration of said iminocarboxylate salt being controlled to 40 to 70 weight %.

However, whereas the iminocarboxylate salt has a structure containing 2 or 3 asymmetric carbon atoms, the aminopolycarboxylate has a structure containing one asymmetric carbon atom; in this respect, these compounds are different in chemical structure. Therefore, there is room for preventing the aminopolycarboxylate from caking and stabilizing the same.

Japanese Kokai Publication Hei-10-87580 discloses a monoaminocarboxylate with a total amount of nitrile compound and amide compound being controlled to 2% or less based on the monoaminocarboxylate. Japanese Kokai Publication Hei-10-87582 discloses a monoaminocarboxylate in which, based on the monoaminocarboxylate, the total amount of cyanide ion, hydrogen cyanide and its salt is controlled to not more than 100 ppm, the total amount of ammonium ion, ammonia and its salt controlled to not more than 1%, and the amount of formaldehyde controlled to not more than 1%.

However, these monoaminocarboxylates have a structure containing one or two asymmetric carbon atoms and are structurally distinct from aminopolycarboxylates. Moreover, as the technology for producing such monoaminocarboxylates, there is disclosed a process which comprises addition of cyanic acid and formaldehyde to the starting material amino acid and subsequent hydrolysis of the resulting addition compound under alkaline conditions, but the monoaminocarboxylate compound obtainable by such a production process has a pH value of about 13.5 to 14 and is not considered to have been sufficiently stabilized. Therefore, there is room for further technological sophistication in order that aminopolycarboxylates may be sufficiently stabilized to facilitate handling, insure long-term maintenance of product quality and, hence, may be adapted to various industrial applications.

SUMMARY OF THE INVENTION

In view of the above state of the art, the present invention has for its object to provide a stabilized aqueous aminopolycarboxylate solution composition and a method of stabilizing the aminopolycarboxylate through preventing the same from caking.

The inventors of the present invention explored in earnest for a technology of stabilizing an aminopolycarboxylate through prevention of caking and found that when the compound is rendered into the form of an aqueous solution, a satisfactory stabilizing effect can be expected. In this case, they encountered several problems: (1) that although it is economical to handle the aminopolycarboxylate with high concentration and at a low temperature, the aminopolycarboxylate crystallizes under such high-concentration, low-temperature conditions, with the degree of precipitation increasing with the lapse of time and, in some cases, the aqueous solution as such may completely solidify, (2) that when the amount of impurity is large, that is to say when the product is of low purity, said precipitation is more liable to occur, (3) that when the viscosity of the aqueous solution exceeds 10 Pa·s, even in the absence of crystallization, the product becomes extremely difficult to handle and cannot be easily applied to many end-uses, and (4) that if an attempt is made to heat an aminopolycarboxylate aqueous solution to increase its concentration to a desirable level, the aminopolycarboxylate aqueous solution is stained to detract from the product value and the aminopolycarboxylate is precipitated.

The inventors found that when the D/L ratio of the aspartic acid skeleton of the aminopolycarboxylate is specified to be not equal to 1:1, the stability of the compound in aqueous solution is improved as compared with a 1:1 mixture (racemic compound) and that if the concentration of solids in an aqueous solution of aminopolycarboxylate and the pH of the aqueous solution are specified, coupled with the effect obtained by specifying the D/L ratio, the aminopolycarboxylate is protected against caking over a prolonged period time and can be provided in the form of an aminopolycarboxylate aqueous solution which is stable and homogeneous substantially without separation of crystals or solidification of the aqueous solution; the inventors thus found that the above-mentioned drawbacks can be neatly overcome. The inventors further discovered that if the content of the polymer and the like which are produced in the production of an aminopolycarboxylate is specified, the viscous precipitate will hardly form, thus allowing the operation and effect of the present invention to be more fully expressed. The present invention has been accordingly developed.

Therefore, the present invention is an aqueous aminopolycarboxylate solution composition containing an aminopolycarboxylate represented by the following general formula (1):

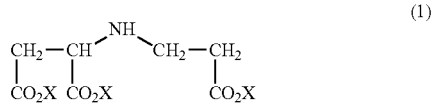

in the formula, X may be the same or different and represents a hydrogen atom, an alkali metal atom, or an ammonium group, which has a D-form/L-form molar ratio of an aspartic acid skeleton of the aminopolycarboxylate of 1/0 to 0.7/0.3 or 0.3/0.7 to 0/1, has a solid concentration of 25 to 60 mass %, and has a pH value of not more than 11.

DISCLOSURE OF THE INVENTION

The present invention is now described in detail.

The aqueous aminopolycarboxylate solution composition according to the present invention contains an aminopolycarboxylate represented by the above-mentioned general formula (1), and can be applied to cases in which such an aminopolycarboxylate is to be made into a stable and homogeneous aqueous solution. In the present invention, the aminopolycarboxylate of the general formula (1) is N-2-carboxyethyl-aspartic acid and/or its salt, and one or two or more of such compounds can be employed.

Referring to the above-mentioned general formula (1), X may be the same or different and represents a hydrogen atom, an alkali metal atom, or an ammonium group. The alkali metal atom is preferably lithium, sodium or potassium, more preferably sodium. The aqueous aminopolycarboxylate solution composition has a D-form/L-form molar ratio of an aspartic acid skeleton of the aminopolycarboxylate of 1/0 to 0.7/0.3 or 0.3/0.7 to 0/1, has a solid concentration of 25 to 60 mass % and, further, has a pH value of not more than 11. The aqueous solution composition is used herein to mean a composition essentially containing an aqueous solution of the aminopolycarboxylate and optionally containing other ingredients.

In the present invention, the aspartic acid skeleton of the aminopolycarboxylate represented by the above-mentioned general formula (1) means the structure represented by the following general formula (2) within the compound of general formula (1).

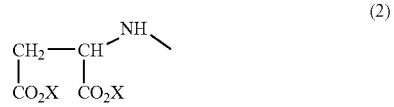

(in the formula, X may be the same or different and represents a hydrogen atom, an alkali metal atom, or an ammonium group.)

The L-form and D-form of the aspartic acid skeleton as used herein mean the compounds whose configuration about the asymmetric carbon in the structure represented by the general formula (2) are S-configured and R-configured; thus the S-configured compound is the L-form and the R-configured compound is the D-form.

Referring to the above aqueous aminopolycarboxylate solution composition, if the ratio of the D-form to the L-form or vice versa of the aspartic acid skeleton of the aminopolycarboxylate deviates from the above-mentioned range, handling of such an aminopolycarboxylate in the form of an aqueous solution composition undergoes separation of crystals within a short time period to give a non-homogeneous slurry and in order that the aqueous solution composition may be handled as a homogeneous slurry, it is not only necessary to provide a special agitation operation such as forced circulation with a pump but also is liable to cause troubles such as pipe clogging during the transfer by pumping. As the isomer ratio of the aspartic acid skeleton, D-form/L-form (molar ratio) is 1/0 to 0.7/0.3 or 0.3/0.7 to 0/1, preferably 1/0 to 0.8/0.2 or 0/1 to 0.2/0.8.

If the solid concentration of the aqueous solution of the aminopolycarboxylate is less than 25 mass %, the aqueous solution can be handled as a stable aqueous solution, but since this is a dilute solution, the equipment for storage and transportation becomes large, thus being economically disadvantageous. If the concentration exceeds 60 mass %, crystals will separate out of the aqueous solution composition to make handling difficult. Within the above-mentioned concentration range, even sodium aminopolycarboxylate can be handled as a stable aqueous solution composition. The more preferred concentration range is not less than 35 mass % and not more than 55 mass % and the still more preferred range is not less than 40 mass % and not more than 50 mass %. The solid referring to the solid concentration includes not only the aminopolycarboxylate but also impurities and salts thereof which will be described hereinafter.

If the pH of the above-mentioned aminopolycarboxylate aqueous solution exceeds pH 11, staining of the aqueous solution and progressive decomposition of the aminopolycarboxylate will take place during storage to lead to product degradation. The pH of the aqueous solution is preferably not lower than 4. If pH is lower than 4, the aminopolycarboxylate is liable to undergo decomposition and crystallize out in aqueous solution to make it difficult to handle the solution as a homogeneous aqueous solution, in some cases. The pH is preferably not higher than 10.5 and not lower than 4.5. More preferably, it is not higher than 10 and not lower than 6.

Referring to the method of pH measurement for use in the present invention, the measuring temperature is preferably 25° C. and measurements can be made with a pH meter using glass composite electrodes. The suitable glass composite electrode is 6366-10D (product name, product of HORIBA, Ltd.) and the preferred pH meter is pH Meter F-22 (product name, product of HORIBA, Ltd.).

The purity of the above-mentioned aminopolycarboxylate can be expressed by the following equation.

Purity(mass %)=(concentration of aminopolycarboxylate/solid concentration)×100

In the aqueous aminopolycarboxylate solution composition according to the present invention, not only aminopolycarboxylates of high purity but also those of low purity in which the aminopolycarboxylate is hitherto crystallized out can be stabilized.

The effect of stabilizing the aqueous aminopolycarboxylate solution composition according to the present invention is remarkable when the purity of the aminopolycarboxylate is 95 mass % or less. The lower limit to the purity of the aminopolycarboxylate in the aqueous aminopolycarboxylate solution composition according to the present invention is suitably not less than 60 mass %. Thus, the aqueous aminopolycarboxylate solution composition according to the present invention is suitable when such an aminopolycarboxylate with such purity is to be made into a stable and homogeneous aqueous solution and, in such cases, the functional effect of the present invention is fully expressed. Thus, when the purity is 90 mass % or less, the effect is more remarkable and when it is 80 mass % or less, the effect is still more outstanding.

As the impurities referred to above, there can be mentioned the unreacted aspartic acid, acrylic polymer, fumaric acid, etc. Among these, fumaric acid and aspartic acid are so low in the solubility in water that these tend to cause precipitation. In accordance with the present invention, even such easily-precipitating impurities are contained, the compound can be stabilized in the form of an aqueous solution free from precipitation.

Regarding the aqueous aminopolycarboxylate solution composition according to the invention, the polymer content is preferably not more than 1 mass % based on the whole aqueous solution. The polymer means a compound contained as an impurity in the composition and if it exceeds 1 mass %, a viscous precipitate is generated during handling the aqueous solution composition to prevent sufficient expression of the functional effect of the invention. The more preferred polymer content is not more than 0.5 mass %.

When, as described below, an acrylic acid compound is used in preparing the aqueous aminopolycarboxylate solution composition, an acrylic polymer tends to form and, therefore, it is preferable to specify the acrylic polymer content as above.

The polymer content referred to above is preferably determined by gel permeation chromatography (GPC). For example, as the column, SHODEX Asahipak GF-7M HQ (product name, product of Showa Denko K. K.) can be used with advantage, and as the carrier, a carrier solution prepared by dissolving 34.5 g of disodium hydrogen phosphate and 46.2 g of sodium dihydrogen phosphate into 5 L of ultra pure water and filtrating the solution with a 0.45 μm membrane filter (product of Advantec Toyo Kaisha, Ltd.) can be used with advantage.

The technology of preparing the above aqueous aminopolycarboxylate solution composition preferably includes (I) the method which comprises reacting a starting material comprising aspartic acid and/or its salt and an acrylic acid compound in an aqueous medium and (II) the method which comprises causing acrylonitrile to add to aspartic acid under alkaline condition and hydrolyzing the obtained reaction compound with an alkali metal hydroxide, and using these methods and the like, an aqueous solution composition containing an aminopolycarboxylate of general formula (1) can be obtained. Among these and other methods, the method (I) is suitable because an aqueous aminopolycarboxylate solution composition having any desired pH can be obtained without increasing the number of production steps.

In the above preparation method (I), the acrylic acid compound is preferably acrylic acid, an acrylic ester, or sodium acrylate, and aspartic acid and/or its salt and said acrylic acid compound may each be used one or two or more species. The ratio of aspartic acid and/or its salt and acrylic acid compound in the starting material as well as the reaction temperature and other reaction conditions are not particularly restricted. The aqueous medium is water or a mixture of water and a solvent soluble in water, and water; and a mixed solvent of water with methanol, ethanol, isopropyl alcohol, acetone or acetonitrile can be used with advantage, although, among these, water is preferably used.

In the above reaction, if the D-form of aspartic acid and/or its salt is used as a starting material, the configuration derived from the same will be retained as R-configuration at the asymmetric carbon atom of the aspartic acid skeleton in the structure of the resulting aminopolycarboxylate so that the product aminopolycarboxylate will be a D-isomer with respect to the aspartic acid skeleton. Such an aminopolycarboxylate can be prepared by the method which comprises adding, to react, an acrylic acid compound to a reaction system comprising aspartic acid whose carboxylic function has been partially or totally neutralized to give an aqueous solution containing an aminopolyaspartic acid. When adding an acrylic acid compound, it is preferable to set the neutralization ratio of carboxylic function of aspartic acid to 60 to 100% and the molar ratio of addition of acrylic acid compound to aspartic acid to 0.8 to 1.2. Moreover, when the acrylic acid compound is added, the reaction system is controlled to a temperature not below 50° C. and the concentration of the acrylic acid compound in the reaction system is adjusted to not more than 10 mass %. Further, by adjusting the pH of the reaction mixture at 11 or below during the reaction or after completion of the reaction, a stable aqueous solution of aminopolycarboxylate free from precipitation can be obtained.

In the above preparation method, it is preferable to add the acrylic acid compound to the reaction system dropwise instead of adding it in the block. In this case, the duration of dropwise addition of the acrylic acid compound is preferably not less than 30 minutes, more preferably 1 hour to 3 hours. Further, the dropwise addition is preferably carried out insuring that the concentration of the acrylic acid compound in the reaction mixture will be not higher than 10 mass % as mentioned above. By such dropwise addition, formation of the polymer during production of the aminopolycarboxylate can be inhibited and the stability of the aqueous aminopolycarboxylate solution composition can be improved.

In the preparation method (II) described above, too, if the D-form of aspartic acid is used as a starting material, the product aminopolycarboxylate will be a D-isomer with respect to the aspartic acid skeleton.

Referring to the above preparation methods (I) and (II), the technology of controlling the isomer ratio of the aspartic acid skeleton of the above aminopolycarboxylate within the above-mentioned range in the production of the aminopolycarboxylate of the general formula (1) preferably includes a method in which the reaction is carried out using a starting material containing aspartic acid and/or its salt whose D/L ratio is within the specified range, and a method which comprises synthesizing the D-form of aminopolycarboxylate and L-form of aminopolycarboxylate independently and blending them in the specified ratio. As the technology of controlling the pH of an aqueous solution containing the aminopolycarboxylate, a starting material containing said aspartic acid and acrylic acid compound to give the aqueous solution having a pH falling within the above-mentioned range may be used, or a basic compound may be used before and/or after the reaction to adjust pH. As the basic compound, alkali metal hydroxides or carbonates and ammonium group-containing compounds are suitable, and such compounds may be used one or two or more species. Among these, sodium hydroxides are preferably used.

While the above aminopolycarboxylate aqueous solution can be obtained by reacting aspartic acid with an acrylic acid compound as mentioned above, for the purpose of preventing precipitation of crystals during the reaction, the reaction can be carried out using the starting material of such a concentration that the concentration of the aminopolycarboxylate in the reaction mixture available on completion of the reaction, namely the product aminopolycarboxylate aqueous solution, is lower than 30 mass %. In this case, it is necessary to concentrate the aminopolycarboxylate aqueous solution by heating so as to give an aqueous solution with a solid concentration of 25 to 60 mass % and a pH value not higher than 11; and this concentration by heating is preferably carried out under reduced pressure at a temperature of 30 to 90° C. and an aqueous solution pH of 4 to 11. At any temperature exceeding 90° C., the aminopolycarboxylate is partially decomposed and stained to seriously detract from its product value. Concentration at a temperature lower than 30° C. is industrially undesirable because, for example, it will call for the use of an increased degree of vacuum. Furthermore, if the pH is less than 4 in carrying out the concentration, the aminopolycarboxylate tends to be decomposed and the occasion for precipitation of the aminopolycarboxylate may possibly increase. If the pH exceeds 11, the aqueous solution will be stained and the decomposition of the aminopolycarboxylate will progress leading to poor product quality, in some cases.

The present invention is further directed to a method of stabilizing an aminopolycarboxylate which comprises using the above-described aqueous aminopolycarboxylate solution composition to stabilize the aminopolycarboxylate.

The stabilizing method mentioned above means that, when the compound to be stabilized is prepared into an aqueous solution form in order to prevent from caking, troubles such as separation of crystals and solidification of the aqueous solution is suppressed over a protracted time period and the solution is rendered to be a fully stable and homogeneous state. This stabilizing method can be applied with advantage to the transportation by means of a tank lorry or the like; storage in a tank or the like; and transportation through a pipeline inclusive of piping, valves, nozzles and the like.

The handling temperature of the aqueous aminopolycarboxylate solution composition according to the invention is not particularly restricted and includes any arbitrary temperatures, however, the functional effect of the stabilizing method according to the invention is prominently expressed particularly when the aqueous aminopolycarboxylate solution composition is handled under rugged temperature conditions, namely at low temperatures from −10 to 10° C. or high temperatures from 30 to 70° C. Thus, handling the above aqueous aminopolycarboxylate solution composition at temperatures from −10 to 10° C. or from 30° C. to 70° C. constitutes one of the preferred embodiments of the present invention. According to the stabilizing method of the invention, the aminopolycarboxylate can be easily handled without encountering separation of crystals from such a concentrated aminopolycarboxylate aqueous solution as above or solidification of the aqueous solution even at a temperature not higher than 10° C. and can be easily handled without decomposition and staining of the aminopolycarboxylate even during prolonged storage at an elevated temperature of not lower than 30° C. If the handling temperature is lower than −10° C., the aqueous solution tends to be drastically decreased in fluidity so that it will hardly be transferred or transported, and if the temperature exceeds 70° C., the aminopolycarboxylate as such tends to be decomposed to cause the decrease in the product purity.

In one of the most preferred modes of carrying out the present invention, the aqueous aminopolycarboxylate solution composition in which the isomer ratio of the aspartic acid skeleton of the aminopolycarboxylate formed by the reaction between aspartic acid and an acrylic acid compound is D/L (molar ratio)=1/0 to 0.7/0.3 or D/L (molar ratio)=0/1 to 0.3/0.7 is concentrated by heating at a temperature of 30 to 90° C. and a solution pH of 4 to 11 to give an aqueous solution composition having a solid concentration of 25 to 60 mass % and a pH value of not more than 11 and this composition is handled at temperatures from 30 to 70° C. In this mode, the staining in the course of concentration can be prevented and the aminopolycarboxylate can be handled as a stable and homogeneous aqueous solution free from separation of crystals and solidification.

Since, by the method of stabilizing an aminopolycarboxylate according to the invention, an aminopolycarboxylate can be consistently handled in the form of a homogeneous aqueous solution, it can be stored in a container without providing any special incubation, agitation and other devices. Moreover, it can be delivered directly from the reactor or storage tank to the destination site via a pipeline, or filled in a tank lorry, tank car, container, drum can, or the like to transport the same. As the gas phase for such storage or transportation, it is preferable to use an inert gas, such as nitrogen or argon gas, or air.

As the constituent material of the storage tank, for instance, which is used in handling the aqueous aminopolycarboxylate solution composition according to the invention, carbon steel, stainless steel, hastelloy steel, titanium-alloyed steel, nickel steel or the like can be used with advantage, and the surface area to contact the aminopolycarboxylate aqueous solution may be lined with glass, a resin such as Teflon, or rubber. Particularly, stainless steel is used with advantage.

By preparing the aminopolycarboxylate in the form of the aqueous solution composition described above according to the invention, the aminopolycarboxylate can be handled as a stabilized aqueous solution, namely, a long-term stable and homogeneous aqueous solution without precipitation of crystals of aminopolycarboxylate and impurities or solidification or separation thereof due to such precipitation. Furthermore, the viscosity of the aqueous aminopolycarboxylate solution composition can be controlled to not more than 10 Pa·s. Such form of an aqueous solution composition, namely an aqueous solution composition with a viscosity of not more than 10 Pa·s can be easily handled and constitutes one preferred embodiment of the invention.

The aqueous aminopolycarboxylate solution composition according to the invention, constituted as above, is a long-term stable and homogeneous aqueous solution composition suppressed for crystallization of the aminopolycarboxylate salt or impurities and solidification or separation of the aqueous solution. Moreover, the method of stabilizing an aminopolycarboxylate of the present invention is a method to stabilize an aqueous aminopolycarboxylate solution composition through prevention of caking thereof.

BEST MODE FOR CARRYING OUT THE INVENTION

The following examples illustrate the present invention in further detail without defining the scope of the invention. Unless otherwise indicated, all "parts" mean "parts by weight" and all "percentages (%)" mean "mass %".

The following equipments were used for the analyses and measurements of the respective components.

Aminopolycarboxylate and impurities other than acrylic polymer: High Performance Liquid Chromatography (HPLC), detector; differential refractometer, ultra violet-visible detector Acrylic polymer: Gel Permeation Chromatography (GPC), column; SHODEX Asahipak GF-7M HQ (product name, product of Showa Denko K.K.)

pH: pH Meter F-22 (product name, product of HORIBA, Ltd.), glass composite electrode; 6366-10D (product name, product of HORIBA, Ltd.)

PRODUCTION EXAMPLE 1

In a mixture of 2.7 kg of water and 4.75 kg of 48% aqueous solution of NaOH was dissolved 4.56 kg of L-aspartic acid. While this solution was stirred at the reflux temperature, 3.06 kg of 80% aqueous solution of acrylic acid was added dropwise over 2 hours. After completion of dropwise addition, the stirring at the reflux temperature was further continued for 6 hours. Then, 3.2 kg of water and 1.69 kg of 48% aqueous solution of NaOH were added and the mixture was cooled to below 40° C.

This solution contained 35 mass % of trisodium N-(2-carboxyethyl)-L-aspartate and 8.8 mass % of impurity. The pH of this solution at 25° C. was 9.7.

PRODUCTION EXAMPLE 2

Except that D-aspartic acid was used in lieu of L-aspartic acid, the procedure of Production Example 1 was repeated to give an aqueous solution containing 35 mass % of trisodium N-(2-carboxyethyl)-D-aspartate and 8.8 mass % of impurity. The pH of this solution at 25° C. was 9.7.

PRODUCTION EXAMPLE 3

In a mixture of 2.7 kg of water and 4.75 kg of 48% aqueous solution of NaOH was dissolved 4.56 kg of L-aspartic acid. While this solution was stirred at the reflux temperature, 3.06 kg of 80% aqueous solution of acrylic acid was added dropwise over 2 hours. After completion of dropwise addition, the stirring at the reflux temperature was further continued for 6 hours. Then, 3.2 kg of water was added and the mixture was cooled to below 40° C.

This solution contained 38.2 mass % of trisodium N-(2-carboxyethyl)-L-aspartate and 9.5 mass % of impurity. The pH of this solution at 25° C. was 5.2.

PRODUCTION EXAMPLE 4

Except that D-aspartic acid was used in lieu of L-aspartic acid, the procedure of Production Example 3 was repeated to give an aqueous solution containing 38.3 mass % of trisodium N-(2-carboxyethyl)-D-aspartate and 9.6 mass % of impurity. The pH of this solution at 25° C. was 5.1.

PRODUCTION EXAMPLE 5

In a mixture of 4000 g of water and 766 g of 48% aqueous solution of NaOH was dissolved 612 g of L-aspartic acid. While this solution was stirred at 30° C., 260 g of acrylonitrile was added dropwise over 1 hour. After completion of dropwise addition, the stirring at 30° C. was further continued for 7 hours. Then, 437 g of 48% aqueous solution of NaOH was added, and the mixture was heated to 108° C. to distill 2440 g of aqueous ammonium out of the system.

This solution contained 33 mass % of trisodium N-(2-carboxyethyl)-L-aspartate and 3.7 mass % of impurity. The pH of this solution at 25° C. was 13.2.

PRODUCTION EXAMPLE 6

Under cooling, 2.7 kg of water was mixed with 4.75 kg of 48% aqueous solution of NaOH and, then, 4.56 kg of L-aspartic acid was dissolved therein. The temperature of this solution was 30° C. With the solution being stirred, 3.06 kg of 80% aqueous solution of acrylic acid was added in the block, and after heating to the reflux temperature, the stirring was further continued for 8 hours. Then, 3.2 kg of water and 1.69 kg of 48% aqueous solution of NaOH were added, and the reaction mixture was cooled to below 40° C. This solution contained 35 mass % of trisodium N-(2-carboxyethyl)-L-aspartate and 8.5 mass % of impurity. Of this amount of impurity, a polymer with a molecular weight of 400000 accounted for 2 mass %. The pH of this solution at 25° C. was 10.

SYNTHESIS EXAMPLE 1

While an aqueous solution prepared in the same manner as in Production Example 6 was stirred, 1000 g of 98% sulfuric acid was gradually added, and the mixture was stirred at 80° C. for one hour. After cooling to room temperature, the white crystals obtained by filtration were washed with water and dried to give 855 g of N-(2-carboxyethyl)-L-aspartic acid.

SYNTHESIS EXAMPLE 2

Except that D-aspartic acid was used in lieu of L-aspartic acid, the procedure of Production Example 6 was repeated to give an aqueous solution containing 33 mass % of trisodium N-(2-carboxyethyl)-D-aspartate and 3.6 mass % of impurity. The pH of this solution at 25° C. was 13.1.

SYNTHESIS EXAMPLE 3

While an aqueous solution prepared in the same manner as in Production Example 5 was stirred, 1000 g of 98% sulfuric acid was gradually added, and the mixture was stirred at 80° C. for one hour. After cooling to room temperature, the white crystals obtained by filtration were washed with water and dried to give 850 g of N-(2-carboxyethyl)-D-aspartic acid.

The samples synthesized in Production Examples 1 to 4 and Synthesis Examples 1 to 3 were blended in arbitrary ratios, followed by addition of NaOH where necessary, and the resulting solutions were tested for storage stability. The results are shown in Table 1.

TABLE 1

| Sample No. | D/L (molar ratio) | Product concentration (mass %) | Impurity (mass %) | Polymer (mass %) | Solid (mass %) | pH at 25° C. | Temperature (° C.) | Precipitate (after 2 months) |
|---|---|---|---|---|---|---|---|---|
| 1 | 0/1 | 35.0 | 8.8 | Not detected | 43.8 | 9.7 | 10 | None |
| 2 | 0/1 | 35.0 | 8.8 | Not detected | 43.8 | 9.7 | 25 | None |
| 3 | 0/1 | 35.0 | 8.8 | Not detected | 43.8 | 9.7 | 40 | None |
| 4 | 0/1 | 35.0 | 8.8 | Not detected | 43.8 | 9.7 | 60 | None |
| 5 | 1/0 | 35.0 | 8.8 | Not detected | 43.8 | 9.7 | 10 | None |
| 6 | 0/1 | 38.2 | 9.5 | Not detected | 47.7 | 5.2 | 25 | None |
| 7 | 0/1 | 38.2 | 9.5 | Not detected | 47.7 | 5.2 | 40 | None |
| 8 | 0/1 | 38.2 | 9.5 | Not detected | 47.7 | 5.2 | 60 | None |
| 9 | 0/1 | 38.2 | 9.5 | Not detected | 47.7 | 5.2 | 10 | None |
| 10 | 1/0 | 38.3 | 9.6 | Not detected | 47.9 | 5.1 | 10 | None |
| 11 | 2/8 | 35.0 | 8.8 | Not detected | 43.8 | 9.7 | 10 | None |
| 12 | 8/2 | 35.0 | 8.8 | Not detected | 43.8 | 9.7 | 10 | None |
| 13 | 2/8 | 38.2 | 9.5 | Not detected | 47.7 | 5.2 | 40 | None |
| 14 | 8/2 | 38.3 | 9.6 | Not detected | 47.9 | 5.1 | 40 | None |
| 15 | 3/7 | 35.0 | 8.8 | Not detected | 43.8 | 9.7 | 10 | None |
| 16 | 7/3 | 35.0 | 8.8 | Not detected | 43.8 | 9.7 | 10 | None |
| 17 | 3/7 | 38.2 | 9.5 | Not detected | 47.7 | 5.2 | 40 | None |
| 18 | 7/3 | 38.3 | 9.6 | Not detected | 47.9 | 5.1 | 40 | None |
| 19 | 0/1 | 40 | 6.4 | Not detected | 46.4 | 4.5 | 25 | None |
| 20 | 0/1 | 40 | 6.4 | Not detected | 46.4 | 4.5 | 40 | None |
| 21 | 0/1 | 40 | 6.4 | Not detected | 46.4 | 4.5 | 60 | None |
| 22 | 0/1 | 40 | 8.3 | Not detected | 48.3 | 7.0 | 10 | None |
| 23 | 0/1 | 40 | 8.3 | Not detected | 48.3 | 7.0 | 25 | None |
| 24 | 0/1 | 40 | 8.3 | Not detected | 48.3 | 7.0 | 40 | None |
| 25 | 0/1 | 40 | 8.3 | Not detected | 48.3 | 7.0 | 60 | None |
| 26 | 0/1 | 40 | 9.5 | Not detected | 49.5 | 8.5 | 10 | None |
| 27 | 0/1 | 40 | 9.5 | Not detected | 49.5 | 8.5 | 25 | None |
| 28 | 0/1 | 40 | 9.5 | Not detected | 49.5 | 8.5 | 40 | None |
| 29 | 0/1 | 40 | 9.5 | Not detected | 49.5 | 8.5 | 60 | None |
| 30 | 0/1 | 40 | 10 | Not detected | 50 | 10.0 | 60 | None |
| 31 | 0/1 | 35.0 | 8.3 | 0.5 | 43.8 | 9.7 | 10 | None |
| 32 | 0/1 | 35.0 | 8.3 | 0.5 | 43.8 | 9.7 | 25 | None |
| 33 | 0/1 | 35.0 | 8.3 | 0.5 | 43.8 | 9.7 | 40 | None |
| 34 | 0/1 | 35.0 | 8.3 | 0.5 | 43.8 | 9.7 | 60 | None |

Using the samples synthesized in Production Examples 5 and 6, the storage stability test was performed. The results are shown in Table 2. The samples synthesized in Synthesis Examples 1 to 3 were appropriately and/or concentrated and tested for storage stability. The results are also shown in Table 2.

TABLE 2

| Sample No. | D/L (molar ratio) | Product concentration (mass %) | Impurity (mass %) | Polymer (mass %) | Solid (mass %) | pH at 25° C. | Temperature (° C.) | Precipitate (after 2 months) |
|---|---|---|---|---|---|---|---|---|
| 35 | 0/1 | 33.0 | 3.7 | Not detected | 36.7 | 13.2 | 25 | White precipitate |
| 36 | 0/1 | 35.0 | 6.5 | 2 | 43.5 | 10 | 25 | Viscous precipitate |
| 37 | 2/8 | 34.5 | 6.2 | 1.9 | 43.8 | 10.2 | 25 | Viscous precipitate |
| 38 | 3/7 | 34.8 | 5.9 | 2.1 | 43.7 | 9.9 | 25 | Viscous precipitate |
| 39 | 4/6 | 35.0 | 8.8 | Not detected | 43.8 | 9.7 | 10 | White precipitate |
| 40 | 6/4 | 35.0 | 8.8 | Not detected | 43.8 | 9.7 | 25 | White precipitate |
| 41 | 5/5 | 35.0 | 8.8 | Not detected | 43.8 | 9.7 | 25 | White precipitate |
| 42 | 5/5 | 38.2 | 9.5 | Not detected | 47.7 | 5.2 | 40 | White precipitate |
| 43 | 0/1 | 55 | 6.1 | Not detected | 61.1 | 9.7 | 25 | White precipitate |
| 44 | 0/1 | 55 | 6.1 | Not detected | 61.1 | 9.7 | 40 | White precipitate |

Referring to Table 2 above, Samples No. 39 to 44 were outside the range of the invention in D-form/L-form ratio; Samples No. 43 to 44 were outside the range of the invention in solid concentration; and Samples No. 35 was outside the range of the invention in pH, and all of these samples were found to be less stable, giving white precipitates after 2 months. For samples No. 36 to 38, Production Example 6 in which the aminopolycarboxylate was synthesized by adding an aqueous solution of acrylic acid in the block was used so that these contained 2 mass % of polymer and this was found to adversely affect the stability.

The invention claimed is:

1. A stabilized, homogeneous and transportable aqueous aminopolycarboxylate solution composition and containing water as a solvent and an aminopolycarboxylate represented by the following general formula (1):

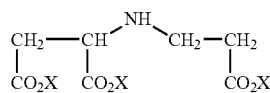
(1)

in the formula, X may be the same or different and represents a hydrogen atom, an alkali metal atom, or an ammonium group, which has a D-form/L-form molar ratio of an aspartic acid skeleton of the aminopolycarboxylate of 1/0 to 0.7/0.3 or 0.3/0.7 to 0/1, has a solid concentration of 25 to 60 mass %, and has a pH value of not more than 11 for stability of the aminocarboxylate solution composition, wherein the aspartic acid skeleton of the aminopolycarboxylate is represented by the following general formula (2) within the compound of general formula (1):

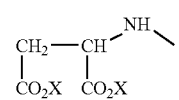
(2)

wherein X may be the same or different and represents a hydrogen atom, an alkali metal atom, or an ammonium group, wherein a polymer content is not more than 1 mass % based on the whole aqueous solution.

2. The aqueous aminopolycarboxylate solution composition according to claim 1,
wherein the solid concentration is 35 to 55 mass %.

3. The aqueous aminopolycarboxylate solution composition according to claim 1,
wherein the solid concentration is 40 to 50 mass %.

4. The aqueous aminopolycarboxylate solution composition according to claim 1,
wherein the pH is not lower than 4.

5. The aqueous aminopolycarboxylate solution composition according to claim 1,
wherein the pH is 4.5 to 10.5.

6. The aqueous aminopolycarboxylate solution composition according to claim 1,
wherein the pH is 6 to 10.

7. The aqueous aminopolycarboxylate solution composition according to claim 1,
wherein the solid concentration is 35 to 55 mass % and the pH is not lower than 4.

8. The aqueous aminopolycarboxylate solution composition according to claim 1,
wherein the solid concentration is 40 to 50 mass % and the pH is 4.5 to 10.5.

9. The aqueous aminopolycarboxylate solution composition according to claim 1,
wherein the solid concentration is 40 to 50 mass % and the pH is 6 to 10.

10. The aqueous aminopolycarboxylate solution composition according to claim 1,
wherein said solid concentration is from 40 to 60 mass %.

* * * * *

UNITED STATES PATENT AND TRADEMARK OFFICE
CERTIFICATE OF CORRECTION

PATENT NO. : 7,319,165 B2  
APPLICATION NO. : 10/458186  
DATED : January 15, 2008  
INVENTOR(S) : Yasutaka Sumida et al.

It is certified that error appears in the above-identified patent and that said Letters Patent is hereby corrected as shown below:

Title Page item 54 and Col. 1
  The title "AMINOPOLYCARBOXYLIC ACID AQUEOUS SOLUTION COMPOSITION AND STABILIZATION METHOD OF ~~AMINOPOLYCARBOXLIC~~ ACID", It should read --AMINOPOLYCARBOXYLIC ACID AQUEOUS SOLUTION COMPOSITION AND STABILIZATION METHOD OF AMINOPOLYCARBOXYLIC ACID--

Signed and Sealed this

Second Day of September, 2008

JON W. DUDAS  
*Director of the United States Patent and Trademark Office*